United States Patent [19]

Rossau et al.

[11] Patent Number: 5,721,097
[45] Date of Patent: Feb. 24, 1998

[54] HYBRIDIZATION PROBES FOR THE DETECTION OF BRANHAMELLA CATARRHALIS STRAINS

[75] Inventors: Rudi Rossau, Ekeren-Antwerpen; Hugo Van Heuverswyn, Kalken, both of Belgium

[73] Assignee: N. V. Innogenetics S.A., Ghent, Belgium

[21] Appl. No.: 299,810

[22] Filed: Sep. 1, 1994

Related U.S. Application Data

[63] Continuation of Ser. No. 934,518, filed as PCT/EP91/00211, Feb. 1, 1991, published as WO91/11531, Aug. 8, 1991, abandoned.

[30] Foreign Application Priority Data

Feb. 2, 1990 [GB] United Kingdom ............... 90400297

[51] Int. Cl.$^6$ ...................................... C12Q 1/68
[52] U.S. Cl. ................ 435/6; 435/91.2; 536/24.32; 536/24.33
[58] Field of Search ................ 435/6, 91.2; 536/24.32, 536/24.33

[56] References Cited

U.S. PATENT DOCUMENTS 4,851,330  7/1989  Kohne ........................................ 435/6

FOREIGN PATENT DOCUMENTS 0 079 139 A1  5/1983  European Pat. Off. .

OTHER PUBLICATIONS

Maniatis et al., Molecular Cloning, Cold Spring Harbor Lab. pp. 387–388 (1982).

Abstracts of the Annual Meeting. p. 124, (1989).

*Primary Examiner*—Scott W. Houtteman
*Attorney, Agent, or Firm*—Merchant, Gould, Smith, Edell, Welter & Schmidt, P.A.

[57] ABSTRACT

Methods of detection of the Gram-negative bacterium, *Branhamella catarrhalis* are disclosed. These methods use nucleic acid hybridization probes derived from the bacterium's ribosomal RNA genes.

14 Claims, 2 Drawing Sheets

FIG. 1A

```
            10         20         30         40         50         60
    1  AGGCTTAACA CATGCAAGTC GAACGAAGTT AGGAAGCTTG CTTCTGATAC TTAGTGGCGG
   61  ACGGGTGAGT AATGCTTAGG AATCTGCCTA GTAGTGGGGG ATAACTTGGG GAAACCCAAG
  121  CTAATACCGC ATACGACCTA CGGGTGAAAG GCTTTTA GCTCTCGCTA TTAGATGAGC
  181  CTAAGTCGGA TTAGCTGGTT GGTGGGGTAA AGGCCTACCA AGGCGACGAT CTGTAGCTGG
  241  TCTGAGAGGA TGATCAGCCA CACTGGGACT GAGACACGGC CCAGACTCCT ACGGGAGGCA
  301  GCAGTGGGGA ATATTGGACA ATGGGCGAAA GCCTGATCCA GCCATGCCGC GTGTGTGAAG
  361  AAGGCCTTTT GGTTGTAAGT CACTTTAAGT GGGGAGGAAA GCCTTATGGT TAATACCCAT
  421  AAGCCCTGAC GTTACCCACA GAATAAGCAC CGGCTAACTC TGTGCCAGCA GCCGCGGTAA
  481  TACAGAGGGT GCAAGCGTTA ATCGGATTAC TGGGCGTAAA GCGCGCGTAG GTGGTTATTT
  541  AAGTCAGATG TGAAAGCCCC GGGCTTAACC TGGGAACTGC ATCTGATACT GGATAACTAG
  601  AGTAGGTGAG AGGGGNGTAG AATTCCAGGT GTAGCGGTGA AATGCGTAGA GATCTGGAGG
  661  AATACCGATG GCGAAGGCAG CTCCCTGGCA TCATACTGAC ACTGAGGTGC GAAAGCGTGG
  721  GTAGCAAACA GGATTAGATA CCCTGGTAGT CCACGCCGTA AACGATGTCT ACCAGTCGTT
  781  GGGTCTTTA AAGACTTAGT GACGCAGTTA ACGCAATAAG TAGACCGCCT GGGGAGTACG
  841  GCCGCAAGGT TAAAACTCAA ATGAATTGAC GGGGCCCGC ACAAGCGGTG GAGCATGTGG
  901  TTTAATTCGA TGCAACGCGA AGAACCTTAC CTGGTCTTGA CATAGTGAGA ATCTTGCAGA
  961  GATGCGAGAG TGCCTTCGGG AATTCACATA CAGGTGCTGC ATGGCTGTCG TCAGCTCGTG
 1021  TCGTGAGATG TTGGGTTAAG TCCCGCAACG AGCGCAACCC TTTTCCTTAG TTACCAGCGA
 1081  CTCGGTCGGG AACTCTAAGG ATACTGCCAG TGACAAACTG GAGGAAGGCG GGGACGACGT
 1141  CAAGTCATCA TGGCCCTTAC GACCAGGGCT ACACACGTGC TACAATGGTT GGTACAAAGG
 1201  GTTGCTACAC AGCGATGTGA TGCTAATCTC AAAAAGCCAA TCGTAGTCCG GATTGGAGTC
 1261  TGCAACTCGA CTCCATGAAG TCGGAATCGC TAGTAATCGC AGATCAGAAT GCTGCGGTGA
 1321  ATACGTTCCC GGGCCTTGTA CACACCGCCC GTCACACCAT GGGAGTTGAT TCACCAGAAG
 1381  GTGGTTAGCC TAACGCAAGA GGGCGATCAC CACGGTGGG GTCACACTG TCGATGACTG
 1441  GTAACAAGGT AGCCGTAGGG GAACTGCGGC TGGATCACCT CCTTA
```

FIG. 1B

```
             10         20         30         40         50         60
             |          |          |          |          |          |
  1  GGTCAAGTAA TGAAGTGCAC ATGGTGGATG CCTTGGCAGT CAGAGGCGAT GAAAGACGTG
 61  ATAGCCTGCG ATAAGCGTCG GTGAGGTGGC AATATCCTGT GACCCGGCGA TTTCTGAATG
121  GGGAAACCCA ACCAACATAA GTTGGTTATT ACACAGTTTA CTGTGTAAGG CAAACCGGGA
181  GAAGTGAAAC ATCTCAGTAC CCCGAGGAAA AGACATCAAA TGAGATTCCG TAAGTAGCGG
241  CGAGCGAACA CGGAGGAGCC GATCAATTTT ACAGTAGCAA AATGGCGTGG GAAAGCCAAC
301  CATAGTAGGT GATAGTCCTG TATGCGAAAC TGTTTAAGCG ACATATTAAG TAGGGCGGAA
361  CACGAGAAAT TCTGTCTGAA GATGGGNNNN CCATCCTCCA AGGCTAAATA CTCCTGACNG
421  ACCGATAGTG A
```

HYBRIDIZATION PROBES FOR THE DETECTION OF BRANHAMELLA CATARRHALIS STRAINS

This is a continuation of application Ser. No. 07/934,518, filed as PCT/EP91/00211 published as WO91/11531 Aug. 8, 1991 now abandoned.

The invention relates to hybridization probes for detecting strains belonging to the species *Branhamella catarrhalis*. Hereafter, the word strains also encompasses isolates or organisms contained in a biological sample.

*Branhamella catarrhalis* is a fastidious Gram-negative bacterium which may be involved in serious infections in human beings. Although diagnostic test procedures for this organism exist, the speed and the specificity of the detection can be considerably improved by using deoxyribonucleic acid (DNA)-probe assays. These DNA probes can, for instance, be total genomic DNA, plasmids, or synthetic oligonucleotides and these probes may target the genomic DNA or messenger or stable ribonucleic acid (RNA) species present in biological samples. Nevertheless, while not the only approach, the use of synthetic oligonucleotides is preferred. The limited length of the oligonucleotides provides extreme specificity; a few mismatches induce a considerable decrease in stability of the probe-target duplex. Oligonucleotides can be rapidly synthesized in large amounts, have a long shelf-life, and are easily purified and labeled.

Species-specific probes have been described for a large number of organisms including *Branhamella catarrhalis* (Beaulieu and Roy, Abstract No. D-249, Annual Meeting of the American Society for Microbiology, 1989).

However, species-specific probes derived from the ribosomal RNA (rRNA) genes of *Branhamella catarrhalis* have not been described.

The aim of the invention is to provide probe sequences deduced from variable regions within the rRNA molecules.

Such probes have an increased sensitivity because ribosomal rRNA molecules are very abundant in a cell as compared with the genome.

However, because of the high conservation of the rRNA gene, it was not expected that specific rRNA derived probes could be obtained which would be specific so as to differentiate the organism concerned from its closest neighbors. That is why for each particular case, the specificity and sensitivity of the probes have to be verified experimentally. RNA-derived probes which could have been thought to be specific for *Branhamella catarrhalis* turned out to be non-specific. For example, and unexpectedly, a species-specific probe for *Branhamella catarrhalis* could not be found in region III or V of the 16S rRNA molecule (as defined in Rossau et al., J. Gen. Microbiol. 135: 1735–1745, 1989), whereas in this same region, specific probes for *Neisseria gonorrhoeae* could be derived. This is quite unexpected because in this respect it is known that there is no organism so similarly related to *Branhamella catarrhalis* as, for instance, *Neisseria gonorrhoeae* is to *Neisseria meningitidis*.

The sequence of the rRNA derived probes is preferably complementary to the rRNA sequence itself, but probes with a sequence identical to the rRNA sequence, and which subsequently target the DNA molecules, can be used as well for specific detection.

These rRNA-directed probes or their complements can also be used to detect fragments obtained by enzymatic amplification of the target sequence concerned.

Thus, an object of the invention is to provide rRNA derived DNA probes for detecting most, if not all, *Branhamella catarrhalis* strains.

Another object of the invention is to provide DNA probes for detecting *Branhamella catarrhalis* strains with a simple hybridization test, such as a dot-spot, a strand-displacement, a sandwich hybridization test, or a competition hybridization, without resorting to any complementary analysis, such as the Southern blot analysis.

Still another object of the invention is to provide probes and a simple method for the in vitro diagnosis of *Branhamella catarrhalis* strains.

"rRNA-related" as used herein refers to the fact that the probes concerned hybridize with sequences normally present in ribosomal RNAs, no matter whether said probes are themselves formed of DNA or RNA fragments, or whether they consist of cloned fragments (in the case of DNA) or of synthetic oligonucleotides.

A hybridization probe of the invention for detecting *Branhamella catarrhalis* strains contains:

either a sequence belonging to a nucleic acid selected from the following groups of nucleic acids and which includes itself with from 15 to the maximum number of nucleotides of the selected nucleic acid,

| Group BC1(SEQ ID NO:1): | |
|---|---|
| TATCAGAAGC AAGCTTCCTA ACTTCGTT | BC1(SEQ.ID NO:1) |
| AACGAAGTTA GGAAGCTTGC TTCTGATA | BC1IC(SEQ.ID NO:2) |
| AACGAAGUUA GGAAGCUUGC UUCUGAUA | BC1ICR(SEQ.ID NO:3) |
| UAUCAGAAGC AAGCUUCCUA ACUUCGUU | BC1R(SEQ.ID NO:4) |
| Group BC2: | |
| TAGCTTGGGT TTCCCCAAGT T | BC2(SEQ.ID NO:5) |
| AACTTGGGGA AACCCAAGCT A | BC2IC(SEQ.ID NO:6) |
| AACUUGGGGA AACCCAAGCU A | BC2ICR(SEQ.ID NO:7) |
| UAGCUUGGGU UUCCCCAAGU U | BC2R(SEQ.ID NO:8) | or a variant sequence which differs from any of the preceding sequences either by:
(i) addition to or removal from any of their respective extremities of one or several nucleotides, or by
(ii) changing of one or more nucleotides within any of said sequences, or by
both (i and ii),
yet provided that in any of the above circumstances the said probe still hybridizes with the same RNA or DNA target as the corresponding unmodified sequence.

Probes targeting rRNA are advantageous over probes which target the genomic DNA such as the probe described by Beaulieu and Roy, since rRNA is single-stranded and consequently directly available for hybridization, and is present in multiple copies in bacterial cells.

In order to obtain the probe sequences of the invention, rRNA genes were enzymatically amplified using the polymerase chain reaction (PCR). Conserved sequences in the 16S or 23S rRNA were used as primers. The amplified fragments were cloned in a plasmid vector and sequenced using the dideoxy chain termination method. This approach is considerably less tedious and time-consuming than the conventional cloning procedures using genomic banks or selected restriction endonuclease fragments. Although rRNA sequences are more rapidly obtained when the sequencing reactions are performed directly on purified rRNA or PCR fragments without cloning, the sequence information generated from cloned fragments is more accurate and complete. Since the strong secondary structure of rRNA molecules introduces many ambiguities within the nucleotide sequences obtained using the dideoxy chain termination method, it is advisable to sequence both strands, which is not possible with purified rRNA. In contrast to PCR fragments, cloned rRNA gene fragments can easily be purified in large amounts, which results in clearly readable sequencing ladders. Since one mismatch in the probe sequence may result in useless probes, accuracy is highly preferred over speed when obtaining rRNA sequences.

In the sequences given in groups BC1 and BC2, the letters stand for the following nucleotides:
A: Adenylic residue
C: Cytidylic residue
G: Guanidylic residue
T: Thymidylic residue
U: Uracylic residue By the expression "target" is meant a sequence complementary to any of the sequences of groups BC1 and BC2, as heretofore defined. In the case where the probe of the invention would comprises nucleic acid elongations on either side or both of said above defined sequences—e.g. nucleic acid fragments of cloning vector or linker fragments resulting from the cleavage of said probe out of said cloning vector—it is understood that such elongations should be selected such as to avoid the possibility that they could themselves hybridize with any other corresponding complementary nucleic acid sequence outside of the above target in a DNA of any microorganism likely to be tested by the process of this invention as later defined. Such hybridization would be of a parasitical nature and reduce the specificity of the probe.

Preferred probes consist of nucleic acid fragments formed of any of the sequences of the groups defined above, with said fragments containing from 15 to the maximum number of nucleotides of the relevant nucleic acid sequence.

It is understood that in the above nucleotide sequences (and in the other ones referred to hereafter), the left end of the formulae always corresponds to a 5' extremity and the right end to a 3' extremity of the sequence concerned.

When reference is further made therein to a "probe of group 'X'"—with 'X' from BC1 or BC2—it should be understood that such probe has a sequence included in one of the nucleic acids belonging to that group as defined above or defined hereinafter.

It is also understood that the word "nucleotide" as used herein refers indistinctly to ribonucleotides and deoxyribonucleotides and modified nucleotides such as inosine unless otherwise specified. The expression "nucleotides" also encompasses those which further comprise modification groups, e.g. chemical modification groups which do not affect their hybridization capabilities. Such modification groups aim, for instance, at facilitating their coupling, either directly or indirectly, with suitable markers or labels for the subsequent detection of the probes so marked or labeled particularly in their hybridization products with the relevant rRNA or DNA strand, e.g. that or those initially contained in a biological sample together with other DNA(s) and/or RNA(s).

For instance, such modification groups are recognizable by antibodies which, in turn, can be recognized specifically by other antibodies, carrying a suitable enzymatic or fluorescent or chemiluminescent label. Possible labeling procedures will be exemplified later hereinafter.

The invention also relates to probes having any of the sequences defined above and in which some nucleotides are different, provided that the different nucleotide(s) do(es) not alter the specificity of the probes defined above. Some probes may consist of one of the nucleic acids belonging to any of the groups which are set forth above or of part thereof, with said probes however including nucleotidic elongation on either sides thereof to the extent that such elongations do no alter the specificity of said probes with the genetic material of *Branhamella catarrhalis*.

The invention thus provides for probes which are either replicas (those designated by numbers followed by "IC" or "ICR") in terms of nucleotide sequence of sequences contained in the RNAs or DNAs of most *Branhamella catarrhalis* strains with occasionally a few insignificant differences in nucleotide sequences or formed of sequences, those designated by bare numbers or by numbers followed by "R", complementary to sequences included in the natural RNAs of *Branhamella catarrhalis*. More particularly, it should be appreciated that the target sequences in the RNAs or DNAs concerned consist in any of the following successive sequences present in most, if not all, *Branhamella catarrhalis* strains, subject to possible insignificant natural differences from one strain to another, whereby such natural differences are not likely to affect the hybridization specificity of the probes of this invention with such targets:
AACGAAGUUA GGAAGCUUGC UUCUGAUA (SEQ ID NO:3)
AACUUGGGGA AACCCAAGCU A (SEQ ID NO:7).

The probes of the invention can also be defined as being of at least 15 oligonucleotides for detecting one or more *Branhamella catarrhalis* strains of which the target comprises at least 15 contiguous nucleotides to the maximum number of oligonucleotides of one of the following nucleic acid sequences:
TATCAGAAGC AAGCTTCCTA ACTTCGTT, or (SEQ ID NO:1)
AACGAAGTTA GGAAGCTTGC TTCTGATA, or (SEQ ID NO:2)
AACGAAGUUA GGAAGCUUGC UUCUGAUA, or (SEQ ID NO:3)
UAUCAGAAGC AAGCUUCCUA ACUUCGUU, or (SEQ ID NO:4)
TAGCTTGGGT TTCCCCAAGT T, or (SEQ ID NO:5)
AACTTGGGGA AACCCAAGCT A, or (SEQ ID NO:6)
AACUUGGGGA AACCCAAGCU A, or (SEQ ID NO:7)
UAGCUUGGGU UUCCCCAAGU U (SEQ ID NO:8).

The maximum length of the probes of the invention is such that there is no cross hybridization with other bacterial taxa and is preferably of about 20 to about 50 oligonucleotides, more preferably of about 30 to about 50 oligonucleotides.

The preferred rRNA derived probes are those which are complementary to the natural rRNAs concerned, for they hybridize both with said RNAs and the corresponding DNA. Yet, those which have sequences included in said rRNAs therefore which will only hybridize with the relevant natural DNAs and therefore are less sensitive than the preceding ones, are also part of the invention.

The probes according to the invention can be formed by cloning of recombinant plasmids containing inserts including the corresponding nucleotide sequences, if need be cleaving the latter out from the cloned plasmids upon using the adequate nucleases and recovering them, e.g. by fractionation according to molecular weights. The probes according to the invention can be also be synthesized chemically, for instance by the conventional phosphotriester method.

The variants defined here above included those hybridization probes for detecting *Branhamella catarrhalis* strains which target one of the sequences defined hereunder or their corresponding complementary sequence, when the hybridization medium, or the wash medium, or both as appropriate are the following:

hybridization medium: containing about 3×SSC, (SSC= 0.15M NaCl, 0.015M sodium citrate, pH 7.0) about 25 mM of phosphate buffer pH 7.1, 20% deionized formamide 0.02% ficoll, 0.02% bovine serum albumin, 0.02% polyvinylpyrrolidone, and about 0.1 mg/ml sheared, denatured salmon sperm DNA, wash medium: containing about 3×SSC, 25 mM phosphate buffer pH 7.1, and 20% deionized formamide, wherein the target sequence and the corresponding relevant hybridization temperature (HT) and wash temperature (WT) respectively are as follows:

AACGAAGUUA GGAAGCUUGC UUCUGAUA (SEQ ID NO:3)

HT and/or WT: 50° C.

AACUUGGGGA AACCCAAGCU A (SEQ ID NO:7)

HT and/or WT: 35° C.

The invention also relates to a process for detecting Branhamella catarrhalis strains in a biological sample, wherein said process comprises contacting said biological sample in which the nucleic acids (DNAs and RNAs) have been made accessible to hybridization, if need be under suitable denaturation conditions, with a probe of the invention under conditions enabling hybridization between the probe and complementary nucleic acids of the strains, which may be present in the sample, and detecting the hybrids possibly formed.

The process of the invention enables the discrimination of Branhamella catarrhalis from any other organism such as yeast, fungi, protozoa, other bacterial strains, human cells which are liable to be present in the sample in which Branhamella catarrhalis is sought.

The process relates to the detection of Branhamella catarrhalis strains being directly in the sample or after the strain has been cultured. The detection of a hybrid can be interpreted as meaning that an infection due to Branhamella catarrhalis was present in the biological sample, when any of the probes of groups BC1 or BC2 is respectively being used.

According to an advantageous embodiment of the invention, in the process for detecting Branhamella catarrhalis strains, the probes used are the ones hybridizing both with DNA globally and RNA of the Branhamella catarrhalis strains, which may be present in the biological sample.

The hybridization conditions can be monitored by relying upon several parameters, e.g. hybridization temperature, the nature and concentration of the components of the media, and the temperature under which the hybrids formed are washed.

The hybridization and wash temperature is limited in upper value, according to the probe (its nucleic acid composition, kind and length) and the maximum hybridization or wash temperature of the probes described herein is about 35° C. to 50° C. At higher temperatures duplexing competes with the dissociation (or denaturation) of the hybrid formed between the probe and the target.

A preferred hybridization medium contains about 3×SSC, (SSC=0.15M NaCl, 0.015M sodium citrate, pH 7.0), about 25 mM of phosphate buffer pH 7.1, and 20% deionized formamide, 0.02% ficoll, 0.02% bovine serum albumin, 0.02% polyvinylpyrrolidone and about 0.1 mg/ml sheared denatured salmon sperm DNA.

A preferred wash medium contains about 3×SSC, 25 mM phosphate buffer pH 7.1 and 20% deionized formamide. Other hybridization or wash media can be used as well.

However, when modifications are introduced, be it either in the probes or in the media, the temperatures at which the probes can be used to obtain the required specificity should be changed according to known relationships, such as those described in the following reference: B. D. Hames and S. J. Higgins, (eds.). Nucleic Acid Hybridization: A Practical Approach, IRL Press, Oxford, U.K., 1985.

The general process for detecting Branhamella catarrhalis strains according to the invention can be carried out by suitably adjusting the hybridization temperature to a value at which hybridization is specific; in such a case, washing under more stringent conditions is not necessary.

According to another embodiment of the process of the invention, the hybridization temperature need not necessarily be adjusted to the value at which hybridization is specific and, in particular, can be lower than the temperature at which hybridization is specific, provided that washing is carried out at a temperature corresponding to the value at which hybridization is specific.

In a process embodiment for detecting Branhamella catarrhalis strains (and for distinguishing them from other bacterial taxa) with a probe of group BC1 the hybridization temperature is suitably adjusted to a range of about 50° C. and/or the wash temperature to a range of about 50° C., the media being those defined above.

In another process embodiment for detecting Branhamella catarrhalis strains the probe used is any from group BC2 above defined, the hybridization temperature is suitably adjusted to a range of about 35° C. and/or the wash temperature to a range of about 35° C.

The invention further relates to a kit for detecting specifically Branhamella catarrhalis strains containing:

at least one probe selected from among any of those that are specific for Branhamella catarrhalis as defined above, i.e. a probe from groups BC1 or BC2;

the buffer or components necessary for producing the buffer enabling an hybridization reaction between these probes and only the DNAs and/or RNAs of a strain of Branhamella catarrhalis to be carried out;

and optionally containing means for detecting the hybrids resulting from the preceding hybridization.

In some particular applications, other probes as those defined above (group BC1 and BC2) can be used for the detection of Branhamella catarrhalis strains by an hybridization procedure.

The following rRNA-derived oligonucleotide probes can be caused to hybridize to most, if not all, Branhamella catarrhalis strains:

Group BC3:

TCTAATAGCG AGAGCTAAAA GCCCCC BC3 (SEQ ID NO:9)

GGGGGCTTTT AGCTCTCGCT ATTAGA BC3IC (SEQ ID NO:10)

GGGGGCUUUU AGCUCUCGCU AUUAGA BC3ICR (SEQ ID NO:11)

UCUAAUAGCG AGAGCUAAAA GCCCCC BC3R (SEQ ID NO:12)

Group BC4:

GTCAGGGCTT ATGGGTATTA ACCATAAGCT T BC4 (SEQ ID NO:13)

AAGCTTATGG TTAATACCCA TAAGCCCTGA C BC4IC (SEQ ID NO:14)

AAGCUUAUGG UUAAUACCCA UAAGCCCUGA C BC4ICR (SEQ ID NO:15)

GUCAGGGCUU AUGGGUAUUA ACCAUAAGCU U BC44R (SEQ ID NO:16)

Group BC5:
CGTCACTAAG TCTTTAAAAG ACCCAACGAC TG BC5 (SEQ ID NO:17)
CAGTCGTTGG GTCTTTTAAA GACTTAGTGA CG BC5IC (SEQ ID NO:18)
CAGUCGUUGG GUCUUUUAAA GACUUAGUGA CG BC5ICR (SEQ ID NO:19)
CGUCACUAAG UCUUUAAAAG ACCCAACGAC UG BC5R (SEQ ID NO:20)
Group BC6:
CTTAATATGT CGCTTAAACA GTT BC6 (SEQ ID NO:21)
AACTGTTTAA GCGACATATT AAG BC6IC (SEQ ID NO:22)
AACUGUUUAA GCGACAUAUU AAG BC6ICR (SEQ ID NO:23)
CUUAAUAUGU CGCUUAAACA GUU BC6R (SEQ ID NO:24)

These probes are new and are also part of the invention.

The preferred hybridization and wash temperatures are 50° C., 50° C., 50° C. and 40° C. for BC3, BC4, BC5, and BC6, respectively, the media being those defined above.

Under the hybridization and wash conditions enabling hybridization with nucleic acids from *Branhamella catarrhalis*, the probes from group BC3 to BC6 also hybridize with nucleic acids from a limited number of non-*Branhamella catarrhalis* strains such as *Moraxella nonliquefaciens*, *Moraxella lacunata*, *Neisseria ovis*, and *Neisseria caviae*. The probes from group BC3 to BC6 can be used for the detection of *Branhamella catarrhalis* strains in specimens where the above mentioned organism are not likely to be found, or can be ruled out by using one or more additional test such as a Gram stain. Also in a sandwich-hybridization format as outlined below, these probes can be convenient for the specific detection of *Branhamella catarrhalis*.

The probes of the invention can be used in a sandwich hybridization system which enhances the specificity of a nucleic acid probe-based assay.

The principle and the use of sandwich hybridizations in a nucleic acid probe-based assay have been already described (e.g.: Dunn and Massel, Cell, 12: 23–36; 1977; Ranki et al., Gene, 21: 77–85; 1983). Although direct hybridization assays have favorable kinetics, sandwich hybridizations are advantageous with respect to a higher signal to noise ratio. Moreover sandwich hybridizations can enhance the specificity of a nucleic acid probe based assay. If properly designed, a sandwich hybridization assay indeed maximizes the specificity of a nucleic acid probe based test when using two probes recognizing two different nucleic acid stretches of one and the same organism.

The only demands which must be met are that both probes (i) hybridize to the same nucleic acid molecule of the target organism and (ii) do not hybridize to the same non-target organisms.

For two given probes I and II, the sandwich hybridization system can be described as follows:
Probe No. I hybridizes to nucleic acid from organisms A and B (not with C);
Probe No. II hybridizes to nucleic acid from organisms A and C (not with B).

Since it is absolutely required that both probes hybridize to the target nucleic acid, a detectable signal will be generated only if nucleic acid from organism A is present in the sample. It is obvious that if one of the probes is specific for the organism to be detected, the other probe can be composed of any specific or non-specific sequence provided that it hybridizes to the same target molecule as the first probe.

The probes of the invention—groups BC1 to BC6—can be combined in a sandwich hybridization assay which is highly specific for *Branhamella catarrhalis*.

An advantageous combination of probes is constituted by probe BC1 and probe BC2. Other advantageous combinations of the probes are such that one of the probes is either BC1 or BC2 and the second probe is chosen from among BC3, BC4, BC5, or BC6, and more preferably from among BC3, BC4, or BC5. In case BC6 is used as one of the probes, the target is genomic DNA.

Hereunder some advantageous combinations and their corresponding hybridization and wash temperatures (HT & WT) are given by way of example and not by way of limitation:

| Probe I | Probe II | HT & WT (°C.) |
|---------|----------|---------------|
| BC1 | BC2 | 35 |
| BC1 | BC3 | 50 |
| BC1 | BC4 | 50 |
| BC1 | BC5 | 50 |
| BC2 | BC3 | 35 |
| BC2 | BC4 | 35 |
| BC2 | BC5 | 35 |

All these combinations have the 16S rRNA molecule as target.

In the sandwich hybridization process the probes can be added simultaneously or not to the biological sample in which the target DNA or RNA is sought.

The invention also relates to a kit for sandwich hybridization assay, for the detection in vitro of *Branhamella catarrhalis* strains in a biological sample, with said kit containing:
- at least one of the probes or one of the combinations of probes specific for the organisms of interest as above defined.
- the buffer or components necessary for producing the buffer enabling hybridization reaction between these probes and the DNAs and/or RNAs of a strain of *Branhamella catarrhalis* to be carried out,
- and optionally containing means for detecting the hybrids resulting from the preceding hybridization.

The oligonucleotides of the invention can be used either as amplification primers in the polymerase chain reaction technique (PCR; Mullis and Faloona, Methods in Enzymology 155:335–350, 1987) to generate specific enzymatically amplified fragments and/or as probes to detect fragments amplified between bracketing oligonucleotide primers.

The specificity of a PCR-assisted hybridization assay can be controlled at different levels.

The amplification process, or the detection process, or both can be specific. The latter case, giving the highest specificity, is preferred. Such a highly specific PCR-assisted test can be developed using the probes of the invention.

Using the probes of groups BC1 and BC2 *Branhamella catarrhalis* strains can be specifically identified using a competition hybridization protocol. In such a test the target nucleic acid is allowed to hybridize either (i) with the detection probe in solution or with (ii) the capture probe bound to a solid support. By monitoring the amount of detection probe that can still be hybridized to the capture probe after the first hybridization has been carried out the presence of target molecules can be determined.

CONDITIONS OF THE USE OF PROBES

The probes of the invention are advantageously labeled. Any conventional label can be used. The probes can be labeled by means of radioactive tracers such as $^{32}P$, $^{35}S$, $^{125}I$, $^{3}H$, and $^{14}C$.

The radioactive labeling can be carried out according to any conventional method such as terminal labeling at the 3' or 5' position with the use of a radiolabeled nucleotide, a polynucleotide kinase (with or without dephosphorylation by a phosphatase), a terminal transferase, or a ligase (according to the extremity to be labeled). One of the probes of the invention can be the matrix for the synthesis of a chain consisting of several radioactive nucleotides or of several radioactive and nonradioactive nucleotides.

The probes of the invention can also be prepared by chemical synthesis using one or several radioactive nucleotides. Another method for radioactive labeling is a chemical iodination of the probes of the invention which leads to the binding of several $^{125}I$ atoms on the probes.

If one of the probes of the invention to be used for hybridization is made radioactive with a nonradioactive RNA or DNA, the method of detecting hybridization will depend on the radioactive tracer used.

Generally, autoradiography, liquid scintillation, gamma counting or any other conventional method enabling one to detect an ionizing ray issued by the radioactive tracer can be used.

Nonradioactive labeling can also be used by associating the probes of the invention with residues having: immunological properties (e.g. antigen or hapten), a specific affinity for some reagents (e.g. ligand), properties providing a detectable enzymatic reaction (e.g. enzyme, co-enzyme, enzyme substrate or substrate taking part in an enzymatic reaction), or physical properties such as fluorescence or emission or absorption of light at any wavelength. Antibodies which specifically detect the hybrids formed by the probe and the target can also be used.

A nonradioactive label can be provided when chemically synthesizing a probe of the invention, the adenosine, guanosine, cytidine, thymidine and uracyl residues thereof being liable to be coupled to other chemical residues enabling the detection of the probe or the hybrids formed between the probe and a complementary DNA or RNA fragment.

However, the nucleotidic sequence of the probe when modified by coupling one or more nucleotides to other chemical residues, would be the same as the nucleotide sequence of one of the probes of the invention.

The invention also relates to processes for detecting RNA and/or DNA with the probes of the invention by hybridization, which have been labeled and can be detected as described above. In this regard, conventional methods of hybridization can be used.

For detecting cells which originate from or are themselves constituting living organisms, the RNA and/or DNA of these cells are made accessible by partial or total lysis of the cells, if need be, using chemical or physical processes, and contacted with one or several probes of the invention which can be detected. This contact can be carried out on an appropriate support such as a nitrocellulose, cellulose, or nylon filter in a livid medium or in solution. This contact can take place under suboptimal, optimal conditions or under restrictive conditions (i.e. conditions enabling hybrid formation only if the sequences are perfectly homologous at a specific stretch of the molecule). Such conditions include temperature, concentration of reactants, the presence of substances lowering the optimal temperature of nucleic acid pairing (e.g. formamide, dimethylsulfoxide and urea) and the presence of substances apparently lowering the reaction volume and/or accelerating hybrid formation (e.g. dextran sulfate, polyethylene glycol or phenol).

The elimination of probe of the invention which has not hybridized can be carried out by washing with a buffer solution of appropriate ionic strength and at an appropriate temperature, with or without treatment with S1 nuclease or any other enzyme digesting single-strand DNA or RNA but not digesting DNA-RNA hybrids or double-strand DNA.

In a liquid medium, the hybrids of the probe of the invention paired to the cellular DNA or RNA fragments can be separated from the rest of the liquid medium in different ways, e.g. by chromatography over hydroxyapatite. Then the hybridized probes are detected by means of the label on the probe.

In order to target the chromosomal DNA fragments carrying the genes coding for the RNA fragments from which the labeled probes of the invention derive, after treating the DNA by one or several enzymes and denaturation of DNA fragments (i.e. separation of both chains), one of the probes of the invention is contacted with the DNA fragments under the conditions enabling hybridization. After the time necessary to get complete the hybridization process, the non-hybridized fragments are separated from the hybridized fragments and the label is detected as has been described above for the detection of the cells.

Generally speaking, the different probes of the invention can also be contained in recombinant DNA, enabling their cloning, if the presence of a heterologous DNA is not a hindrance for the specificity of the probes in the encompassed uses.

BRIEF DESCRIPTION OF THE DRAWINGS

FIGS. 1A and 1B represent the partial nucleotide sequence of the cloned rRNA gene of *Branhamella catarrhalis* ITG 4197. More precisely, the linear conformation from 5' to 3' corresponds to the nucleotide sequence of the upper (sense) strand of the rRNA gene, with FIG. 1A corresponding to a partial sequence of the 16S rRNA (SEQ ID NO:27) gene and FIG. 1B corresponding to a partial sequence of the 23S rRNA gene (SEQ ID NO:28).

The strain of *Branhamella catarrhalis* used is *Branhamella catarrhalis* ITG 4197 which is available at the Institute of Tropical Medicine in Antwerp, Belgium. Probes of groups BC1 to BC5 are derived from the 16S rRNA gene, whereas probes of group BC6 are derived from the 23S rRNA gene.

EXAMPLES

The examples hereafter relate to the preparation of the probes of the invention, the experimental results with respect to the specificity and sensitivity of the probes and their use for diagnostic purposes.

The methods used are essentially the same as described by Rossau et al., J. Gen. Microbiol.; 135: 1735–1745, 1989; or in the European patent application No. 8940/- 045.3 unless otherwise stated.

The enzymatic amplification of rRNA gene fragments of about 500 to 4500 base pairs was obtained by the polymerase chain reaction (PCR) technique performed according to the recommendations given in the "Gene Amp" kit of Perkin Elmer Cetus. Oligonucleotides corresponding to conserved or semi-conserved regions in the rRNA molecules were used as PCR primers.

*Branhamella catarrhalis*, also known as *Moraxella catarrhalis* or *Neisseria catarrhalis*, is a fastidious bacterium which is rather inert biochemically. Its important pathogenic potential has been recognized recently. *Branhamella catarrhalis* seems to be frequently involved in serious infections of the respiratory tract. The diagnosis of *Branhamella catarrhalis* requires culture of the organism, which may be hampered by overgrowth caused by less fastidious microorganisms, and a battery of phenotypical tests to distinguish this organisms from commensals such as *Neisseria* species present in the oral cavity.

In some instances the phenotypical test are inconclusive as to the identity of the presumptive *Branhamella catarrhalis* isolate since there are only a limited number of tests which differentiate *Branhamella catarrhalis* from phenotypically similar bacteria. The use of a DNA probe based assay may considerably simplify the laboratory diagnosis of *Branhamella catarrhalis*.

Moreover, there is some heterogeneity within the species *Branhamella catarrhalis* which can be recognized using the probes of the invention.

1. Detection using dot-blot hybridization

Part of the rRNA gene of *Branhamella catarrhalis* ITG 4197 was enzymatically amplified by the PCR technique and cloned in a plasmid vector. The fragment was subsequently sequenced by the dideoxy chain termination technique. The sequence is shown in FIG. 1. Oligonucleotide sequences of the non-conserved areas of the rRNA genes were selected. The following oligonucleotides were chemically synthesized:

| | |
|---|---|
| TATCAGAAGC AAGCTTCCTA ACTTCGTT | BC1(SEQ.ID NO:1) |
| TAGCTTGGGT TTCCCCAAGT T | BC2(SEQ.ID NO:5) |
| TCTAATAGCG AGAGCTAAAA GCCCCC | BC3(SEQ.ID NO:9) |

The oligonucleotides were $^{32}$P-labeled at their 5' ends or tailed at their 3' ends with digoxigenine labeled UTP using terminal transferase and used as hybridization probes.

As target, dot-spotted denatured genomical DNA or lysed cellular material (immobilized on nylon membranes) from a large number of *Branhamella catarrhalis* strains obtained from different locations as well as several strains of other bacterial taxa was used. The hybridization mixture used was either 3×SSC, 25 mM potassium phosphate buffer, pH 7, deionized formamide (20%, v/v), ficoll (0.02%, w/v), bovine serum albumin (0.02%, w/v), polyvinylpyrrolidone (0.02%, w/v) and sheared, denatured salmon sperm DNA (0.1 mg ml$^{-1}$), or the solution given in the protocol sheet of the nonradioactive DNA labeling and detection kit (Boehringer Mannheim) except that 3×SSC (1×SSC is: 0.15M NaCl, 0.015M sodium citrate, pH 7.0) instead of 5×SSC was used and formamide was added up to 20% (v/v). The wash solution contained 3×SSC, 20% formamide, and 25 mM phosphate buffer pH 7.1.

The hybridization results with these probes are summarized below. The hybridization and wash temperatures were 50° C. for BC1 and BC3 and 35° C. for BC2 using the media defined above.

| | No. positive strains/No. strains tested | | |
|---|---|---|---|
| Taxon | BC1 | BC2 | BC3 |
| Unequivocal *B. catarrhalis* strains | 61/61 | 30/30 | 61/61 |
| Aberrant *B. catarrhalis* strains: | | | |
| NCTC 4103 | 1/1 | 1/1 | 0/1 |
| N7 | 0/1 | 1/1 | 0/1 |
| 018B | 0/1 | 1/1 | 0/1 |
| U33/U34 | 0/1 | 1/1 | 0/1 |
| Non-*B. catarrhalis* strains | 0/22 | 0/21 | 4/21 |

Unequivocal *Branhamella catarrhalis* strains are strains which exhibit phenotypical traits which do not deviate from those of *Branhamella catarrhalis* as described in Bergey's Manual of Systematic Bacteriology (Vol. I, Williams & Wilkins Co. Baltimore pp. 288–309) and which have high total DNA:DNA hybridization homologies with the *Branhamella catarrhalis* type strain (ATCC 25238).

The aberrant *Branhamella catarrhalis* strains are those strains which were received as *Branhamella catarrhalis* strains but were found to be different from the unequivocal strains with respect to the genotype and phenotype. The exact taxonomic status of these strains remains to be determined. However, using some of the probes of the invention, the aberrant strains can be identified and distinguished from other organisms as indicated in the table below:

| | Hybridization with | | |
|---|---|---|---|
| Groups | BC1 | BC2 | BC3 |
| 1. Unequivocal *B. catarrhalis* strains | + | + | + |
| 2. strain NCTC 4103 | + | + | − |
| 3. strains N7, 018B and U33/U34 | − | + | − |
| 4. Non-*B. catarrhalis* strains | − | − | −/+ |

The non-*Branhamella catarrhalis* strains tested are:

| | |
|---|---|
| *Moraxella lacunata* | ATCC 17967 |
| *Moraxella lacunata* | ATCC 17952 |
| *Moraxella bovis* | ITG 1601 |
| *Moraxella nonliquefaciens* | ATCC 19975 |
| *Neisseria cuniculi* | ITG 3388 |
| *Neisseria ovis* | NCTC 11227 |
| *Neisseria caviae* | ATCC 14659 |
| *Alysiella* sp. | ATCC 29468 |
| *Moraxella osloensis* | LMG 1043 |
| *Moraxella osloensis* | ATCC 17974 |
| "*Moraxella paraphenylpyruvica*" | LMG 5125 |
| "*Moraxella camembertii*" | LMG 7022 |
| *Psychrobacter immobilis* | LMG 6784 |
| *Acinetobacter calcoaceticus* | ATCC 23055 |
| *Escherichia coli* | B |
| *Escherichia coli* | MC 1061 |
| *Haemophilus influenza* | NCTC 8143 |
| *Eikenella corrodens* | NCTC 10596 |
| *Xanthomonas maltophilia* | LMG 958 |
| *Xanthomonas campestris* | LMG 568 |
| *Neisseria* sp. | D12 |
| *Neisseria* sp. | S17 |

2. Detection of rRNA using sandwich-hybridization rRNA extracted from *Branhamella catarrhalis* ITM 4197 was hybridized with an oligonucleotide probe with the following sequence:

5'-ACTGCTGCCTCCCGTAGGAGTCTGG-3'(SEQ ID NO:25)

which was bound to the surface of a microtiter plate well. The hybridization was done for 1½ h at 60° C. in the hybridization mixture defined above (point 1) from which formamide was omitted. The wells were washed 3 to 4 times with 300 µl phosphate buffered saline with 0.05% Tween-20 (PBS/Tween). The 200 µl hybridization mix containing 2 pmol digoxigenine labeled probe BC1 was added and hybridization was done at 60° C. for 1 h. Washing was performed at the same stringency for 20 min. The detection protocol as described in the Boehringer labeling and detection kit was followed except that paranitrophenyl-phosphate (3.6 mg/ml) was used as substrate for alkaline phosphatase.

The results (OD reading at 405 nm) after 1 h of colordevelopment are given in the table below:

| fmol RNA | OD 405 |
|---|---|
| 240 | 2.050 |
| 180 | 2.036 |
| 120 | 2.199 |
| 60 | 1.377 |
| 30 | 1.179 |
| 10 | 0.968 |
| 6 | 0.925 |
| 0 (blank) | 0.884 |

Thirty fmol rRNA can be reliably detected using a nonradioactive sandwich hybridization format in microtiter plate wells.

3. Detection of *Branhamella catarrhalis* cells using a competition hybridization assay Serial dilutions of cells of *Branhamella catarrhalis* ITM 4197 were made in Heart Infusion Broth (Difco). The cells were lysed by addition of sodium dodecyl sulfate to a final concentration of 0.5%. Simultaneously aliquots of the same dilutions were plated on blood agar plates for cell count [expressed as CFU (Colony forming units)].

The composition of the solution was adjusted to 3×SSC, 25 mM phosphate buffer pH 7.1 and 0.05 pmol of digoxigenine labeled probe BC1 was added. The hybridization proceeded for 3 h at 60° C. after which the mixture was transferred to a microtiter plate well in which a probe complementary in sequence to probe BC1 was fixed to the surface. A further incubation was done at 60° C. for 1 h. After washing the wells, the detection was performed as described in point 2 here above.

The results of the optical readings after 1 h of color development are shown in the table below:

| CFU | OD 405 | ratio (sample/positive control) |
|---|---|---|
| 0 | 2.351 | (1.00) |
| $2 \times 10^2$ | 2.424 | 1.03 |
| $2 \times 10^3$ | 2.522 | 1.07 |
| $2 \times 10^4$ | 2.514 | 1.07 |
| $2 \times 10^5$ | 2.005 | 0.85 |

Since a drop in signal of 10% or more is significant in this kind of test, $2 \times 10^5$ CFU of *Branhamella catarrhalis* cells could be detected. No significant detection was obtained for $2 \times 10^4$ CFU or less (ratios>0.90).

4. Detection of *Branhamella catarrhalis* using PCR and competition hybridization One ng genomical DNA of *Branhamella catarrhalis* (ITM 4197) was enzymatically amplified with the following primers:

5'-TGGCTCAGATTGAACGCTGGCGGC-3' (SEQ ID NO:26)
5'-TCTAATAGCGAGAGCTAAAAGCCCCC-3' (SEQ ID NO:9)

in a total volume of 100 μl.

Thirty cycles consisting of 1 min denaturation at 95° C., 1 min annealing at 50° C. and 1 min elongation at 72° C. were performed.

The presence of specifically amplified material was determined using a competition hybridization protocol with digoxigenine labeled probe BC1 as described in point 3.

The results after ½ h of color development are shown in the table below:

| μl of PCR mix used | OD 405 | ratio (sample/control) |
|---|---|---|
| 0 | 0.790 | (1.00) |
| 5 | 0.769 | 0.97 |
| 10 | 0.659 | 0.83 |
| 15 | 0.639 | 0.81 |

From these figures it is obvious that a significant positive signal was obtained when 10 and 15 μl of the PCR mix was used.

We claim:

1. A probe for detecting one or more *Branhamella catarrhalis* strains, said probe consisting of a nucleic acid sequence selected from the group of SEQ ID NO:1, SEQ ID NO:2, SEQ ID NO:3, SEQ ID NO:4, SEQ ID NO:5, SEQ ID NO:6, SEQ ID NO:7, and SEQ ID NO:8.

2. A rRNA related probe for detecting one or more *Branhamella catarrhalis* strains, consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

3. A nucleic acid probe of at least 15 nucleotides in length for detecting one or more *Branhamella catarrhalis* strains hybridizing to a target consisting of at least 15 contiguous nucleotides to the maximum number of nucleotides of one of the following nucleic acid sequences: SEQ ID NO:1, SEQ ID NO:2, SEQ ID NO:3 or SEQ ID NO:4.

4. A nucleic acid probe of at least 15 nucleotides in length for detecting one or more *Branhamella catarrhalis* strains hybridizing to a target consisting of at least 15 contiguous nucleotides to the maximum number of nucleotides of one of the following nucleic acid sequences: SEQ ID NO:5, SEQ ID NO:6, SEQ ID NO:7, or SEQ ID NO:8.

5. A process for detecting *Branhamella catarrhalis* strains in a biological sample comprising the steps of:

contacting said biological sample in which the nucleic acids of the strains have been made accessible to hybridization with:

a rRNA related probe consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7 or SEQ ID NO:8; or a probe hybridizing to a target sequence consisting of at least 15 contiguous nucleotides to the maximum number of nucleotides of one of the following nucleic acid sequences: SEQ ID NO:1, SEQ ID NO:2, SEQ ID NO:3 or SEQ ID NO:4; or a probe hybridizing to a target sequence consisting of at least 15 contiguous nucleotides to the maximum number of nucleotides of one of the following nucleic acid sequences: SEQ ID NO:5, SEQ ID NO:6, SEQ ID NO:7 or SEQ ID NO:8;

wherein said contacting is under conditions enabling hybridization between the probe and complementary nucleic acids of *Branhamella catarrhalis* strains; and detecting the hybrids formed.

6. The process for detecting *Branhamella catarrhalis* according to claim 5, wherein the process further comprises hybridization medium and wash medium as follows:

said hybridization medium contains 3×0.15M NaCl, 0.015M sodium citrate at pH 7.0, 2.5 mM phosphate buffer at pH 7.1, 20% deionized formamide, 0.02% ficoll, 0.02% bovine serum albumin, 0.02% polyvinylpyrrolidone and 0.1 mg/ml sheared denatured salmon sperm DNA; and said wash medium contains 3×0.15M NaCl, 0.015M sodium citrate at pH 7.0, 25 mM phosphate buffer at pH 7.1, and 20% deionized formamide; and wherein for target sequence SEQ ID NO:3 hybridization temperature or wash temperature is 50° C.; and for target sequence SEQ ID NO:7 hybridization or wash temperature is 35° C.

7. The process for detecting *Branhamella catarrhalis* according to claim 5, wherein the probes hybridize with DNA and RNA of *Branhamella catarrhalis* strains.

8. The process for detecting *Branhamella catarrhalis* according to claim 5, wherein the process further comprises hybridization medium and wash medium as follows:

said hybridization medium contains 3×0.15M NaCl, 0.015M sodium citrate at pH 7.0, 25 mM phosphate buffer at pH 7.1, 20% deionized formamide, 0.02% ficoll, 0.02% bovine serum albumin, 0.02% polyvinylpyrrolidone and 0.1 mg/ml sheared denatured salmon sperm DNA; and said wash medium contains 3×0.15M NaCl, 0.015M sodium citrate at pH 7.0, 25 mM phosphate buffer at pH 7.1, and 20% deionized formamide; and wherein the probe used is:

a probe consisting of at least 15 contiguous nucleotides to the maximum number of nucleotides of one of the following nucleic acid sequences: SEQ ID NO:1, SEQ ID NO:2, SEQ ID NO:3, or SEQ ID NO:4; or a probe hybridizing to a target consisting of at least 15 contiguous nucleotides to the maximum number of nucleotides of one of the following nucleic acid sequences: SEQ ID NO:1, SEQ ID NO:2, SEQ ID NO:3, or SEQ ID NO:4 with hybridization temperature adjusted to about 50° C. and wash temperature adjusted to about 50° C.; or a probe consisting of a sequence of at least 15 contiguous nucleotides to the maximum number of nucleotides of one of the following nucleic acid sequences: SEQ ID NO:5, SEQ ID NO:6, SEQ ID NO:7, or SEQ ID NO:8; or a probe hybridizing to a target sequence consisting of at least 15 contiguous nucleotides to the maximum number of nucleotides of one of the following nucleic acid sequences: SEQ ID NO:5, SEQ ID NO:6, SEQ ID NO:7, or SEQ ID NO:8 with hybridization temperature adjusted to about 35° C. and wash temperature adjusted to about 35° C.

9. A process for detecting *Branhamella catarrhalis* strains, comprising the steps of:

contacting a biological sample in which nucleic acids have been made accessible to hybridization with two rRNA related probes targeting the same nucleic acid molecule, wherein at least one first probe is specific for *Branhamella catarrhalis* with said first probe being from a group of:

a probe consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8; or a probe hybridizing to a target consisting of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8; and with a second probe from the same group as the first probe or from the following probes: SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24;

wherein said contacting is under hybridization and washing conditions to ensure specific hybridization with complementary nucleic acids of the *Branhamella catarrhalis* strains which are present in the sample, but not with complementary DNA or RNA of other organisms; and using the following hybridization and wash temperatures for the following probe combinations:

probes of group BC1 and probes of group BC2: hybridization and wash temperature: about 35° C.;

probes of group BC1 and probes of group BC3: hybridization and wash temperature: about 50° C.;

probes of group BC1 and probes of group BC4: hybridization and wash temperature: about 50° C.;

probes of group BC1 and probes of group BC5: hybridization and wash temperature: about 50° C.;

probes of group BC2 and probes of group BC3: hybridization and wash temperature: about 35° C.;

probes of group BC2 and probes of group BC4: hybridization and wash temperature: about 35° C.; and probes of group BC2 and probes of group BC5:

hybridization and wash temperature: about 35° C.; and detecting the hybrids formed;

wherein the groups of probes are defined as follows:

Group BC1: derived from SEQ ID NOS:1 to 4;
Group BC2: derived from SEQ ID NOS:5 to 8;
Group BC3: derived from SEQ ID NOS:9 to 12;
Group BC4: derived from SEQ ID NOS:13 to 16;
Group BC5: derived from SEQ ID NOS:17 to 20; and
Group BC6: derived from SEQ ID NOS:21 to 29.

10. A process for detecting *Branhamella catarrhalis* strains comprising the steps of amplifying *Branhamella catarrhalis* nucleic acids using the polymerase chain reaction in which at least one sequence used as an amplification primer or a detection probe of the amplified product is:

(a) a probe consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8; or (b) a probe hybridizing to a target consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

11. A process for detecting *Branhamella catarrhalis* strains in a competition hybridization protocol using probes of claim 2 comprising the steps of:

hybridizing a target nucleic acid with a detection probe in solution or with a capture probe bound to a solid support; and monitoring the amount of detection probe that is hybridized to the capture probe after the first hybridization has been carried out.

12. A kit for the detection in vitro of *Branhamella catarrhalis* strains in a biological sample said kit comprising:

at least one rRNA related probe consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8; or a rRNA related probe hybridizing to a target consisting of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8;

buffer or components necessary for producing the buffer enabling a hybridization reaction between these probes and the DNAs or RNAs of a strain of *Branhamella catarrhalis*; and means for detecting the hybrids.

13. A kit for a sandwich hybridization assay to detect in vitro *Branhamella catarrhalis* strains in a biological sample, wherein said kit comprises:

at least two rRNA related probes targeting the same nucleic acid molecule, with at least one probe specific for *Branhamella catarrhalis*, wherein said probe is:

a probe consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8; or a probe hybridizing to a target consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8;

buffer or components necessary for producing the buffer enabling a hybridization reaction between these probes and the DNAs or RNAs of a strain of *Branhamella catarrhalis*; and means for detecting the hybrids.

14. A kit for detecting *Branhamella catarrhalis* strains using the polymerase chain reaction technique, said kit comprising:

at least one rRNA related probe consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8; or a probe hybridizing to a target consisting of a sequence of at least 15 contiguous nucleotides to the maximum number of nucleotides of one of the following nucleic acid sequences: SEQ ID NO:1, SEQ ID NO:2, SEQ ID NO:3, SEQ ID NO:4, SEQ ID NO:5, SEQ ID NO:6, SEQ ID NO:7, or SEQ ID NO:8;

wherein said probe is used as an amplification primer or a detection probe of the amplified product.

* * * * *

UNITED STATES PATENT AND TRADEMARK OFFICE
CERTIFICATE OF CORRECTION

PATENT NO.    : 5,721,097
DATED         : February 24, 1998
INVENTOR(S)   : Rossau et al It is certified that error appears in the above-identified patent and that said Letters Patent is hereby corrected as shown below:

Column 4,
Line 7: "no" should read -- not -- .

Column 7,
Line 41: "Massel" should read -- Hassel

Column 10,
Line 34-35: "(Seq ID No. 27) gene" should read -- gene (Seq ID No: 27) --

Column 11,
Line 29: "P-labeled" should read -- $^{32}$P-labeled --

Column 31, claim 6,
Line 42, "or" should read -- and --
Line 43, "or" should read -- and --

Column 33, claim 9,
Line 10, "29" should read -- 24 --

Signed and Sealed this

Fourth Day of September, 2001

*Attest:*

*Nicholas P. Godici*

NICHOLAS P. GODICI
*Attesting Officer*     *Acting Director of the United States Patent and Trademark Office*

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Branhamella catarrhalis ( v i i ) IMMEDIATE SOURCE:
( B ) CLONE: Hybridization probe BC1

( x i ) SEQUENCE DESCRIPTION: SEQ ID NO:1:

TATCAGAAGC AAGCTTCCTA ACTTCGTT    28

( 2 ) INFORMATION FOR SEQ ID NO:2:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Branhamella catarrhalis ( v i i ) IMMEDIATE SOURCE:
( B ) CLONE: Hybridization probe BC1IC ( x i ) SEQUENCE DESCRIPTION: SEQ ID NO:2:

AACGAAGTTA GGAAGCTTGC TTCTGATA                       28

( 2 ) INFORMATION FOR SEQ ID NO:3:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Branhamella catarrhalis ( v i i ) IMMEDIATE SOURCE:
( B ) CLONE: BC1ICR ( x i ) SEQUENCE DESCRIPTION: SEQ ID NO:3:

AACGAAGUUA GGAAGCUUGC UUCUGAUA                       28

( 2 ) INFORMATION FOR SEQ ID NO:4:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Branhamella catarrhalis ( v i i ) IMMEDIATE SOURCE:
( B ) CLONE: Hybridization probe BC1R ( x i ) SEQUENCE DESCRIPTION: SEQ ID NO:4:

UAUCAGAAGC AAGCUUCCUA ACUUCGUU                       28

( 2 ) INFORMATION FOR SEQ ID NO:5:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Branhamella catarrhalis ( v i i ) IMMEDIATE SOURCE:
( B ) CLONE: Hybridization probe BC2

( x i ) SEQUENCE DESCRIPTION: SEQ ID NO:5:

TAGCTTGGGT TTCCCCAAGT T                                                                     21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Branhamella catarrhalis ( v i i ) IMMEDIATE SOURCE:
        ( B ) CLONE: Hybridization probe BC2IC ( x i ) SEQUENCE DESCRIPTION: SEQ ID NO:6:

AACTTGGGGA AACCCAAGCT A                                                                     21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Branhamella catarrhalis ( v i i ) IMMEDIATE SOURCE:
        ( B ) CLONE: Hybridization probe BC2ICR ( x i ) SEQUENCE DESCRIPTION: SEQ ID NO:7:

AACUUGGGGA AACCCAAGCU A                                                                     21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Branhamella catarrhalis ( v i i ) IMMEDIATE SOURCE:
        ( B ) CLONE: Hybridization probe BC2R ( x i ) SEQUENCE DESCRIPTION: SEQ ID NO:8:

UAGCUUGGGU UUCCCCAAGU U                                                                     21

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Branhamella catarrhalis (vii) IMMEDIATE SOURCE:
    (B) CLONE: Hybridization probe BC3

(xi) SEQUENCE DESCRIPTION: SEQ ID NO:9:

TCTAATAGCG AGAGCTAAAA GCCCCC         26

(2) INFORMATION FOR SEQ ID NO:10:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Branhamella catarrhalis (vii) IMMEDIATE SOURCE:
    (B) CLONE: Hybridization probe B3IC (xi) SEQUENCE DESCRIPTION: SEQ ID NO:10:

GGGGGCTTTT AGCTCTCGCT ATTAGA         26

(2) INFORMATION FOR SEQ ID NO:11:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: rRNA (vi) ORIGINAL SOURCE:
    (A) ORGANISM: Branhamella catarrhalis (vii) IMMEDIATE SOURCE:
    (B) CLONE: Hybridization probe BC3ICR (xi) SEQUENCE DESCRIPTION: SEQ ID NO:11:

GGGGGCUUUU AGCUCUCGCU AUUAGA         26

(2) INFORMATION FOR SEQ ID NO:12:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: rRNA (vi) ORIGINAL SOURCE:
    (A) ORGANISM: Branhamella catarrhalis (vii) IMMEDIATE SOURCE:
    (B) CLONE: Hybridization probe BC3R (xi) SEQUENCE DESCRIPTION: SEQ ID NO:12:

UCUAAUAGCG AGAGCUAAAA GCCCCC         26

(2) INFORMATION FOR SEQ ID NO:13:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (i i) MOLECULE TYPE: DNA (genomic)

(v i) ORIGINAL SOURCE:
    (A) ORGANISM: Branhamella catarrhalis (v i i) IMMEDIATE SOURCE:
    (B) CLONE: Hybridization probe BC4

(x i) SEQUENCE DESCRIPTION: SEQ ID NO:13:

GTCAGGGCTT ATGGGTATTA ACCATAAGCT T    31

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: DNA (genomic)

(v i) ORIGINAL SOURCE:
        (A) ORGANISM: Branhamella catarrhalis (v i i) IMMEDIATE SOURCE:
        (B) CLONE: Hybridization probe BC4IC (x i) SEQUENCE DESCRIPTION: SEQ ID NO:14:

AAGCTTATGG TTAATACCCA TAAGCCCTGA C    31

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: Branhamella catarrhalis (v i i) IMMEDIATE SOURCE:
        (B) CLONE: Hybridization probe BC4ICR (x i) SEQUENCE DESCRIPTION: SEQ ID NO:15:

AAGCUUAUGG UUAAUACCCA UAAGCCCUGA C    31

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: Branhamella catarrhalis (v i i) IMMEDIATE SOURCE:
        (B) CLONE: Hybridization probe BC44R (x i) SEQUENCE DESCRIPTION: SEQ ID NO:16:

GUCAGGGCUU AUGGGUAUUA ACCAUAAGCU U    31

(2) INFORMATION FOR SEQ ID NO:17:

(i) SEQUENCE CHARACTERISTICS:
        (A) LENGTH: 32 base pairs ( B ) TYPE: nucleic acid
                    ( C ) STRANDEDNESS: single
                    ( D ) TOPOLOGY: linear ( i i ) MOLECULE TYPE: DNA (genomic)

( v i ) ORIGINAL SOURCE:
                    ( A ) ORGANISM: Branhamella catarrhalis ( v i i ) IMMEDIATE SOURCE:
                    ( B ) CLONE: Hybridization probe BC5

( x i ) SEQUENCE DESCRIPTION: SEQ ID NO:17:

CGTCACTAAG TCTTTAAAAG ACCCAACGAC TG                                        3 2

( 2 ) INFORMATION FOR SEQ ID NO:18:

( i ) SEQUENCE CHARACTERISTICS:
                    ( A ) LENGTH: 32 base pairs
                    ( B ) TYPE: nucleic acid
                    ( C ) STRANDEDNESS: single
                    ( D ) TOPOLOGY: linear ( i i ) MOLECULE TYPE: DNA (genomic)

( v i ) ORIGINAL SOURCE:
                    ( A ) ORGANISM: Branhamella catarrhalis ( v i i ) IMMEDIATE SOURCE:
                    ( B ) CLONE: Hybridization probe BC5IC ( x i ) SEQUENCE DESCRIPTION: SEQ ID NO:18:

CAGTCGTTGG GTCTTTTAAA GACTTAGTGA CG                                        3 2

( 2 ) INFORMATION FOR SEQ ID NO:19:

( i ) SEQUENCE CHARACTERISTICS:
                    ( A ) LENGTH: 32 base pairs
                    ( B ) TYPE: nucleic acid
                    ( C ) STRANDEDNESS: single
                    ( D ) TOPOLOGY: linear ( i i ) MOLECULE TYPE: rRNA ( v i ) ORIGINAL SOURCE:
                    ( A ) ORGANISM: Branhamella catarrhalis ( v i i ) IMMEDIATE SOURCE:
                    ( B ) CLONE: Hybridization probe BC5ICR ( x i ) SEQUENCE DESCRIPTION: SEQ ID NO:19:

CAGUCGUUGG GUCUUUUAAA GACUUAGUGA CG                                        3 2

( 2 ) INFORMATION FOR SEQ ID NO:20:

( i ) SEQUENCE CHARACTERISTICS:
                    ( A ) LENGTH: 32 base pairs
                    ( B ) TYPE: nucleic acid
                    ( C ) STRANDEDNESS: single
                    ( D ) TOPOLOGY: linear ( i i ) MOLECULE TYPE: rRNA ( v i ) ORIGINAL SOURCE:
                    ( A ) ORGANISM: Branhamella catarrhalis ( v i i ) IMMEDIATE SOURCE:
                    ( B ) CLONE: Hybridization probe BC5R ( x i ) SEQUENCE DESCRIPTION: SEQ ID NO:20:

CGUCACUAAG UCUUUAAAAG ACCCAACGAC UG                                        3 2

( 2 ) INFORMATION FOR SEQ ID NO:21:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Branhamella catarrhalis ( v i i ) IMMEDIATE SOURCE:
        ( B ) CLONE: Hybridization probe BC6

( x i ) SEQUENCE DESCRIPTION: SEQ ID NO:21:

CTTAATATGT CGCTTAAACA GTT         23

( 2 ) INFORMATION FOR SEQ ID NO:22:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Branhamella catarrhalis ( v i i ) IMMEDIATE SOURCE:
        ( B ) CLONE: Hybridization probe BC6IC ( x i ) SEQUENCE DESCRIPTION: SEQ ID NO:22:

AACTGTTTAA GCGACATATT AAG         23

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Branhamella catarrhalis ( v i i ) IMMEDIATE SOURCE:
        ( B ) CLONE: Hybridization probe BC6ICR ( x i ) SEQUENCE DESCRIPTION: SEQ ID NO:23:

AACUGUUUAA GCGACAUAUU AAG         23

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Branhamella catarrhalis ( v i i ) IMMEDIATE SOURCE:
        ( B ) CLONE: Hybridization probe BC6R ( x i ) SEQUENCE DESCRIPTION: SEQ ID NO:24:

CUUAAUAUGU CGCUUAAACA GUU                                                    23

( 2 ) INFORMATION FOR SEQ ID NO:25:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Branhamella catarrhalis ITM 4197

( x i ) SEQUENCE DESCRIPTION: SEQ ID NO:25:

ACTGCTGCCT CCCGTAGGAG TCTGG                                                  25

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Branhamella catarrhalis ITM 4197

( v i i ) IMMEDIATE SOURCE:
        ( B ) CLONE: PCR primer ( x i ) SEQUENCE DESCRIPTION: SEQ ID NO:26:

TGGCTCAGAT TGAACGCTGG CGGC                                                   24

( 2 ) INFORMATION FOR SEQ ID NO:27:

( i ) SEQUENCE CHARACTERISTICS:
        ( A ) LENGTH: 1485 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Branhamella catarrhalis ( v i i ) IMMEDIATE SOURCE:
        ( B ) CLONE: 16S rRNA Gene ( x i ) SEQUENCE DESCRIPTION: SEQ ID NO:27:

AGGCTTAACA CATGCAAGTC GAACGAAGTT AGGAAGCTTG CTTCTGATAC TTAGTGGCGG    60

ACGGGTGAGT AATGCTTAGG AATCTGCCTA GTAGTGGGGG ATAACTTGGG GAAACCCAAG   120

CTAATACCGC ATACGACCTA CGGGTGAAAG GGGGCTTTTA GCTCTCGCTA TTAGATGAGC   180

CTAAGTCGGA TTAGCTGGTT GGTGGGGTAA AGGCCTACCA AGGCGACGAT CTGTAGCTGG   240

TCTGAGAGGA TGATCAGCCA CACTGGGACT GAGACACGGC CCAGACTCCT ACGGGAGGCA   300

GCAGTGGGGA ATATTGGACA ATGGGCGAAA GCCTGATCCA GCCATGCCGC GTGTGTGAAG   360

AAGGCCTTTT GGTTGTAAAG CACTTTAAGT GGGGAGGAAA AGCTTATGGT TAATACCCAT   420

AAGCCCTGAC GTTACCCACA GAATAAGCAC CGGCTAACTC TGTGCCAGCA GCCGCGGTAA   480

TACAGAGGGT GCAAGCGTTA ATCGGATTAC TGGGCGTAAA GCGCGCGTAG GTGGTTATTT   540

AAGTCAGATG TGAAAGCCCC GGGCTTAACC TGGGAACTGC ATCTGATACT GGATAACTAG   600

```
                                                        -continued

AGTAGGTGAG  AGGGGNGTAG  AATTCCAGGT  GTAGCGGTGA  AATGCGTAGA  GATCTGGAGG  660

AATACCGATG  GCGAAGGCAG  CTCCCTGGCA  TCATACTGAC  ACTGAGGTGC  GAAAGCGTGG  720

GTAGCAAACA  GGATTAGATA  CCCTGGTAGT  CCACGCCGTA  AACGATGTCT  ACCAGTCGTT  780

GGGTCTTTTA  AAGACTTAGT  GACGCAGTTA  ACGCAATAAG  TAGACCGCCT  GGGGAGTACG  840

GCCGCAAGGT  TAAAACTCAA  ATGAATTGAC  GGGGGCCCGC  ACAAGCGGTG  GAGCATGTGG  900

TTTAATTCGA  TGCAACGCGA  AGAACCTTAC  CTGGTCTTGA  CATAGTGAGA  ATCTTGCAGA  960

GATGCGAGAG  TGCCTTCGGG  AATTCACATA  CAGGTGCTGC  ATGGCTGTCG  TCAGCTCGTG  1020

TCGTGAGATG  TTGGGTTAAG  TCCCGCAACG  AGCGCAACCC  TTTTCCTTAG  TTACCAGCGA  1080

CTCGGTCGGG  AACTCTAAGG  ATACTGCCAG  TGACAAACTG  GAGGAAGGCG  GGGACGACGT  1140

CAAGTCATCA  TGGCCCTTAC  GACCAGGGCT  ACACACGTGC  TACAATGGTT  GGTACAAAGG  1200

GTTGCTACAC  AGCGATGTGA  TGCTAATCTC  AAAAAGCCAA  TCGTAGTCCG  GATTGGAGTC  1260

TGCAACTCGA  CTCCATGAAG  TCGGAATCGC  TAGTAATCGC  AGATCAGAAT  GCTGCGGTGA  1320

ATACGTTCCC  GGGCCTTGTA  CACACCGCCC  GTCACACCAT  GGGAGTTGAT  CTCACCAGAA  1380

GTGGTTAGCC  TAACGCAAGA  GGGCGATCAC  CACGGTGGGG  TCGATGACTG  GGGTGAAGTC  1440

GTAACAAGGT  AGCCGTAGGG  GAACTGCGGC  TGGATCACCT  CCTTA                   1485

( 2 ) INFORMATION FOR SEQ ID NO:28:

( i ) SEQUENCE CHARACTERISTICS:
            ( A ) LENGTH: 431 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Branhamella catarrhalis ITG 4197

( v i i ) IMMEDIATE SOURCE:
            ( B ) CLONE: 23S rRNA Gene ( x i ) SEQUENCE DESCRIPTION: SEQ ID NO:28:

GGTCAAGTAA  TGAAGTGCAC  ATGGTGGATG  CCTTGGCAGT  CAGAGGCGAT  GAAAGACGTG  60

ATAGCCTGCG  ATAAGCGTCG  GTGAGGTGGC  AATATCCTGT  GACCCGGCGA  TTTCTGAATG  120

GGGAAACCCA  ACCAACATAA  GTTGGTTATT  ACACAGTTTA  CTGTGTAAGG  CAAACCGGGA  180

GAAGTGAAAC  ATCTCAGTAC  CCCGAGGAAA  AGACATCAAA  TGAGATTCCG  TAAGTAGCGG  240

CGAGCGAACA  CGGAGGAGCC  GATCAATTTT  ACAGTAGCAA  AATGGCGTGG  GAAAGCCAAC  300

CATAGTAGGT  GATAGTCCTG  TATGCGAAAC  TGTTTAAGCG  ACATATTAAG  TAGGGCGGAA  360

CACGAGAAAT  TCTGTCTGAA  GATGGGNNNN  CCATCCTCCA  AGGCTAAATA  CTCCTGACNG  420

ACCGATAGTG  A                                                          431
```